(12) United States Patent
Hall et al.

(10) Patent No.: US 10,139,381 B2
(45) Date of Patent: Nov. 27, 2018

(54) TOILET FOR FILTERING AND ANALYZING GAS COMPONENTS OF EXCRETIA

(71) Applicants: David R. Hall, Provo, UT (US); Dan Allen, Springville, UT (US); Steven Butala, Provo, UT (US); Andrew Davis, Provo, UT (US); Justin Robinson, Provo, UT (US)

(72) Inventors: David R. Hall, Provo, UT (US); Dan Allen, Springville, UT (US); Steven Butala, Provo, UT (US); Andrew Davis, Provo, UT (US); Justin Robinson, Provo, UT (US)

( * ) Notice: Subject to any disclaimer, the term of this patent is extended or adjusted under 35 U.S.C. 154(b) by 10 days.

(21) Appl. No.: 15/352,043

(22) Filed: Nov. 15, 2016

(65) Prior Publication Data

US 2018/0135287 A1 May 17, 2018

(51) Int. Cl.
*G01N 33/00* (2006.01)
*B01D 53/06* (2006.01)
*E03D 9/05* (2006.01)

(52) U.S. Cl.
CPC ......... *G01N 33/0047* (2013.01); *B01D 53/06* (2013.01); *E03D 9/05* (2013.01); *B01D 2253/308* (2013.01); *B01D 2257/708* (2013.01)

(58) Field of Classification Search
CPC ... E03C 9/052; B01D 53/06; B01D 2253/308; B01D 2257/708; G01N 33/0047
USPC .......................................................... 4/216
See application file for complete search history.

(56) References Cited

U.S. PATENT DOCUMENTS

| | | | | |
|---|---|---|---|---|
| 3,763,505 A | * | 10/1973 | Zimmerman | E03D 9/052 4/213 |
| 4,876,748 A | * | 10/1989 | Chun | E03D 9/052 4/213 |
| 5,125,119 A | * | 6/1992 | Munoz | E03D 9/052 4/213 |
| 5,288,306 A | * | 2/1994 | Aibe | B01D 53/02 95/141 |
| 5,829,066 A | * | 11/1998 | Aibe | E03D 9/052 4/213 |
| 6,003,157 A | * | 12/1999 | Bruyere | E03D 9/052 15/327.6 |
| 2005/0262817 A1 | * | 12/2005 | Hatanaka | F01N 3/0212 55/282.3 |
| 2007/0256219 A1 | * | 11/2007 | Ellinger | E03D 9/052 4/213 |
| 2010/0199413 A1 | * | 8/2010 | Pollack | E03D 9/052 4/213 |
| 2012/0219462 A1 | * | 8/2012 | Nozaki | F24F 3/16 422/122 |
| 2013/0205484 A1 | * | 8/2013 | Taciuc | E03D 9/052 4/209 R |
| 2014/0304903 A1 | * | 10/2014 | Cogswell | E03D 9/052 4/314 |

* cited by examiner

*Primary Examiner* — Benjamin R Shaw

(57) ABSTRACT

A toilet is disclosed which, in general, includes a toilet bowl and a housing. The toilet bowl includes multiple apertures and a blower, wherein the blower is fluidly connected to one or more of the apertures. The housing is fluidly connected to the blower. The housing includes a gas permeable substrate and a gas chemical sensor. The gas permeable substrate comprises a first side, a second side, intercalated sorbent media, and a rapid desorption heater.

1 Claim, 13 Drawing Sheets

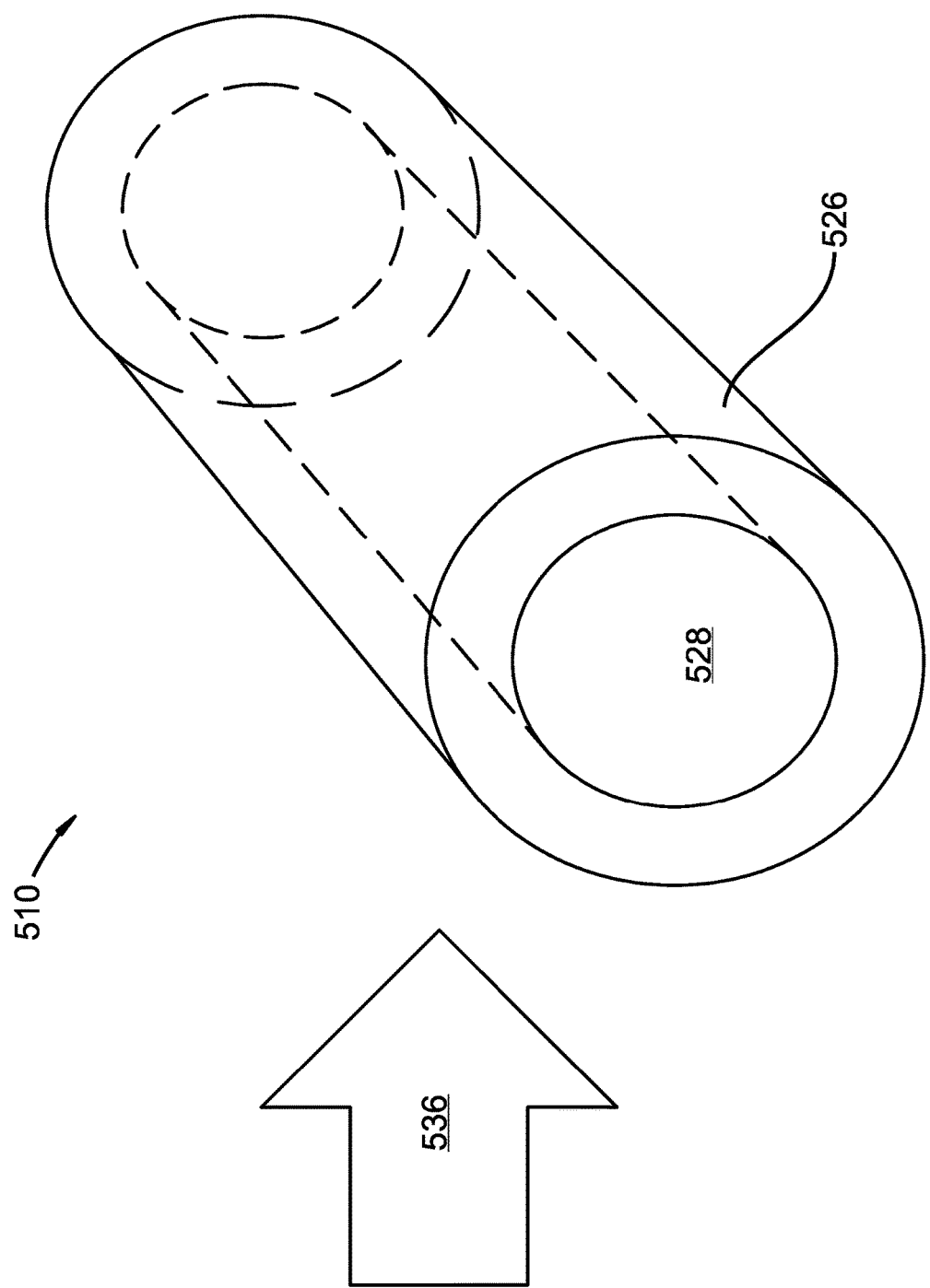

TOILET FOR FILTERING AND ANALYZING GAS COMPONENTS OF EXCRETIA

BACKGROUND

Field of the Invention

This invention relates generally to the field of medical toilets, and more specifically to toilets filtering gas components of excreta.

SUMMARY OF THE INVENTION

An invention has been developed in response to present state of the art and, in particular, in response to problems and needs in the art that have not yet been fully solved by currently available systems and methods. Accordingly, a toilet which filters has been developed. Features and advantages of different embodiments of the invention will become more fully apparent from the following description and appended claims, or may be learned by practice of the invention as set forth hereinafter.

A toilet is disclosed which, in general, includes a toilet bowl and a housing. The toilet bowl includes multiple apertures and a blower, wherein the blower is fluidly connected to one or more of the apertures. The housing is fluidly connected to the blower. The housing includes a gas permeable substrate and a gas chemical sensor. The gas permeable substrate comprises a first side, a second side, intercalated sorbent media, and a rapid desorption heater.

The first side of the gas permeable substrate may be separated from the second side of the gas permeable substrate by a thickness. The gas permeable substrate may include a width which is more than twice the thickness of the gas permeable substrate. The sorbent media may include pore structure having a mean pore size smaller than one micron.

The sorbent media may be intercalated on the first side of the gas permeable substrate, forming a first sorbent-laden side. The sorbent media may also be intercalated on the second side of the gas permeable substrate, forming a second sorbent-laden side. The first sorbent-laden side may be covered by a gas permeable cover. The gas permeable substrate may be oriented with the first sorbent-laden side facing upstream of a flow of gas. The gas permeable substrate may be oriented with the first sorbent-laden side facing downstream of a flow of gas. The gas permeable cover may include same material as the gas permeable substrate, which may include additional sorbent media intercalated into the gas permeable cover.

The sorbent media may be intercalated throughout the gas permeable substrate. The gas permeable substrate may be rotatable about an axis perpendicular to a flow of gas caused by the blower. The gas permeable substrate may have a tubular geometry with the first side being an outer surface and the second side being an inner surface. The rapid desorption heater may be an induction heater and the gas permeable substrate may be ferrous. The rapid desorption heater may be a flash lamp heater, which may include a flash tube. The rapid desorption heater may be a resistance heater.

The gas permeable substrate may be a first gas permeable substrate, the housing may further include a second gas permeable substrate placed in parallel with the first gas permeable substrate. The gas chemical sensor may be a first gas chemical sensor, and the housing may further include a second gas chemical sensor with a different chemical sensitivity than the first chemical sensor placed in parallel with the first gas chemical sensor. The gas permeable substrate may be a first gas permeable substrate, the housing further including a second gas permeable substrate placed in series with the first gas permeable substrate. Rapid desorption heater may be a first heater, and second gas permeable substrate may include a second heater.

The toilet may include a chemical separator. The toilet may further include an array of gas chemical sensors having differing chemical sensitivities.

BRIEF DESCRIPTION OF THE DRAWINGS

A more particular description of the invention briefly described above is made below by reference to specific embodiments. Several embodiments are depicted in drawings included with this application, in which:

FIG. 5 depicts a perspective view of a tubular gas permeable substrate.

DETAILED DESCRIPTION

A detailed description of the claimed invention is provided below by example, with reference to embodiments in the appended figures. Those of skill in the art will recognize that the components of the invention as described by example in the figures below could be arranged and designed in a wide variety of different configurations. Thus, the detailed description of the embodiments in the figures is merely representative of embodiments of the invention, and is not intended to limit the scope of the invention as claimed.

Figure 1A:
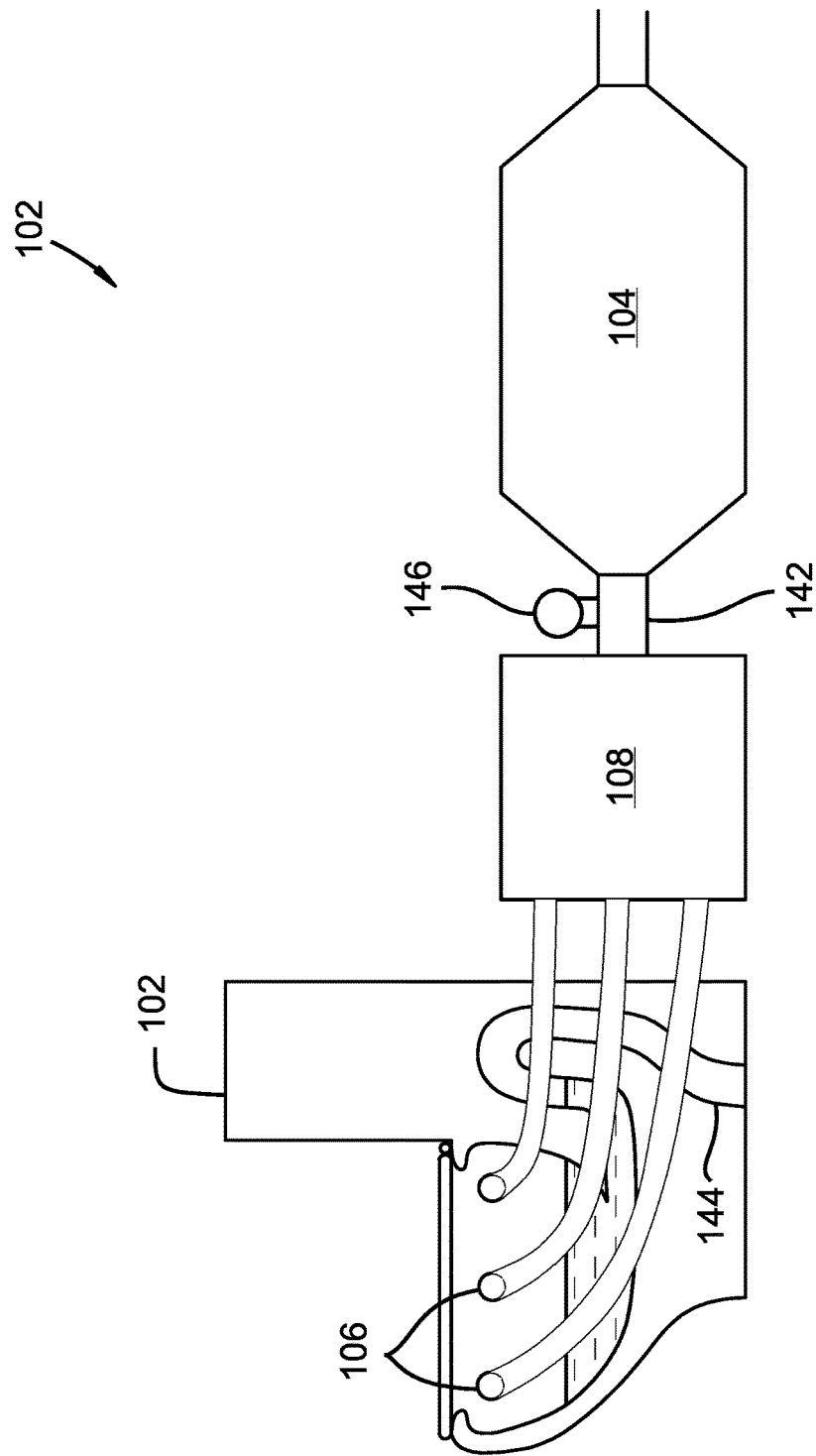
FIG. 1A depicts a side view of an embodiment having a toilet, a blower, and a filtration housing.
Figure 1B:
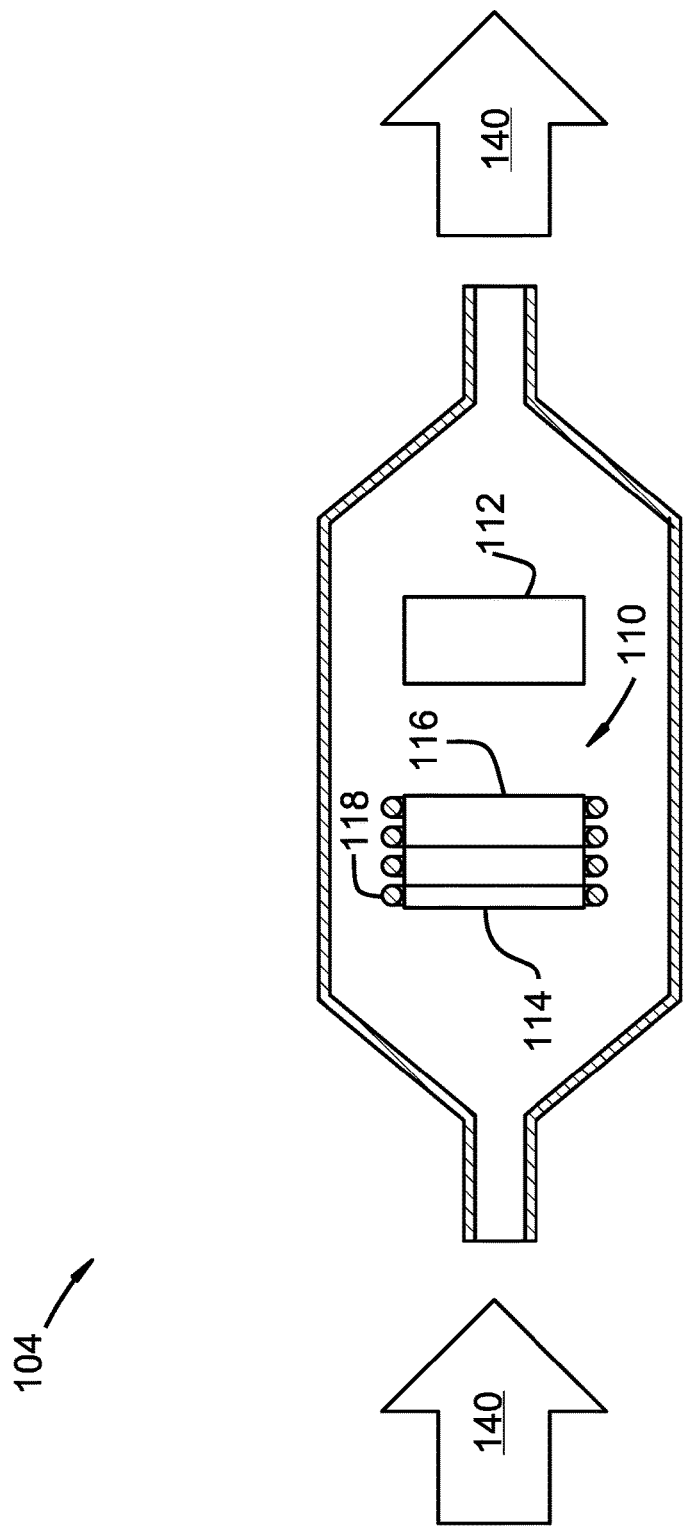
FIG. 1B depicts a cross-sectional side view of a filtration housing and components thereof.

FIG. 1A depicts a side view of an embodiment having a toilet, a blower, and a filtration housing. FIG. 1B depicts a cross-sectional side view of a filtration housing and components thereof. As shown in FIG. 1A, toilet apparatus 100 includes toilet bowl 102 and housing 104. Toilet bowl 102 includes multiple apertures 106 and blower 108. Blower 108 is fluidly connected to one or more of apertures 106, and housing 104 is fluidly connected to blower 108. As shown in FIG. 1B, housing 104 includes gas permeable substrate 110 and gas chemical sensor 112. Gas permeable substrate 110 includes first side 114, second side 116, intercalated sorbent media (depicted in an embodiment described below), and rapid desorption heater 118.

The one or more of apertures 106 fluidly connected to blower 108 may be connected via tubes, piping, or by other fluid conducting means. In some embodiments, toilet bowl 102 may include piping, being integral to the bowl, which may fluidly connect blower 108 and the one or more of apertures 106 which fluidly connect with blower 108.

For example, in some embodiments, a user may deposit excreta into toilet bowl 102. Blower 108 may activate, creating a pressure difference which may cause gasses present in toilet bowl 106 to flow through piping, through blower 108, and through housing 104. Sorbent media included in substrate 110 may adsorb volatile organic compounds (VOCs) present in gasses as the gasses pass through housing 104. Rapid desorption heater 118 may subsequently activate, heating substrate 110 such that VOCs adsorbed by the sorbent media may be released. Gas chemical sensor 112 may then measure the VOCs for one or more chemicals which may have been present within the gasses. Among others, chemicals which chemical sensor 112 may measure for may include perchloroethylene, hydrocarbons, or ammonia.

Housing 104 may also include piping which vents into a vent pipe. In some embodiments, toilet 102 may include trapway 144, wherein air may flow out of housing 104 and into trapway 144. A section of piping 142, toilet 102, or housing 104 may also include valve 146 in order to prevent sewage gases from flowing into housing 104.

Gas chemical sensor 112 may be any of a variety of gas chemical sensors, including a metal oxide sensor, an electrochemical sensor, an acoustic resonator, an optical spectrometer, a chemiresistor, a mass spectrometer, or a flame ionization detector.

Substrate 110 may be oriented such that gas may flow perpendicular to first side 114. However, in some embodiments, substrate 110 may be oriented such that first side 114 is parallel or non-perpendicular with respect to gas flow 140; this may be desirable based on a number of factors, including velocity of gas flow 140, desired particulate concentration, sorbent media intercalation depth, or width, height, and depth of substrate 110.

In some embodiments, substrate 110 may have a width and height to match those of a cross section of housing 104 such that any of gas flow 140 passing through housing 104 must pass through substrate 110. In other words, substrate 110 may have dimensions such that it covers an entire cross-section of housing 104 which is approximately perpendicular to gas flow 140 passing through housing 104.

Sorbent media may be intercalated on first side 114 of substrate 110 forming a first sorbent-laden side. Sorbent media may also be intercalated on second side 116 of substrate 110 forming a second sorbent-laden side. In some embodiments, the first and second sorbent-laden sides may be parallel to gas flow 140, such that both the first and second sorbent-laden sides may capture VOCs with same or different intercalated sorbent media. Sorbent media may be made of a variety of materials, including activated charcoal, silica gel, or organic porous polymers. In some embodiments, the first sorbent-laden side may be intercalated with activated charcoal, while the second sorbent-laden side may be intercalated with silica an organic porous polymer. In some embodiments, substrate 110 may be oriented with the first sorbent-laden side facing upstream of gas flow 140. In some other embodiments, substrate 110 may be oriented with the first sorbent-laden side facing downstream of gas flow 140.

Gas permeable substrate 110 may be rotatable about an axis perpendicular to gas flow 140 caused by blower 108. This may enable variable orientation of substrate 114 with respect to housing 104. In some embodiments, substrate 110 is oriented perpendicular to gas flow 140. Over a period of time, the sorbent media included in substrate 110 may capture VOCs. After the period of time, substrate 110 may be rotated about an axis perpendicular to the flow of gas until it has rotated approximately 180 degrees with respect to its original position. Subsequently, heater 118 may activate, causing the sorbent media to dump VOCs adsorbed nearly simultaneously such that a concentration of the VOCs dumped may be greater than an average concentration contained within gas flow 140, facilitating chemical sensing via gas chemical sensor 112.

Rapid desorption heater 118 may be an induction heater and gas permeable substrate 110 may be ferrous. For example, in some embodiments, heater 118 may be an induction heater which may be attached around an outside surface of housing 104. In some embodiments, heater 118 may be an induction heater contained within housing 104, wherein heater 118 is separated by a distance from substrate 110, such that heater 118 may not contaminate a flow of gas through housing 104.

In some embodiments, rapid desorption heater 118 may be a flash lamp heater. Heater 118 may include a flash tube which may emit a flash of light, thus heating substrate 110 and the sorbent media with sufficient power (energy per unit time) to dump VOCs simultaneously. In some embodiments, rapid desorption heater 118 may be a resistance heater.

Figure 2A:
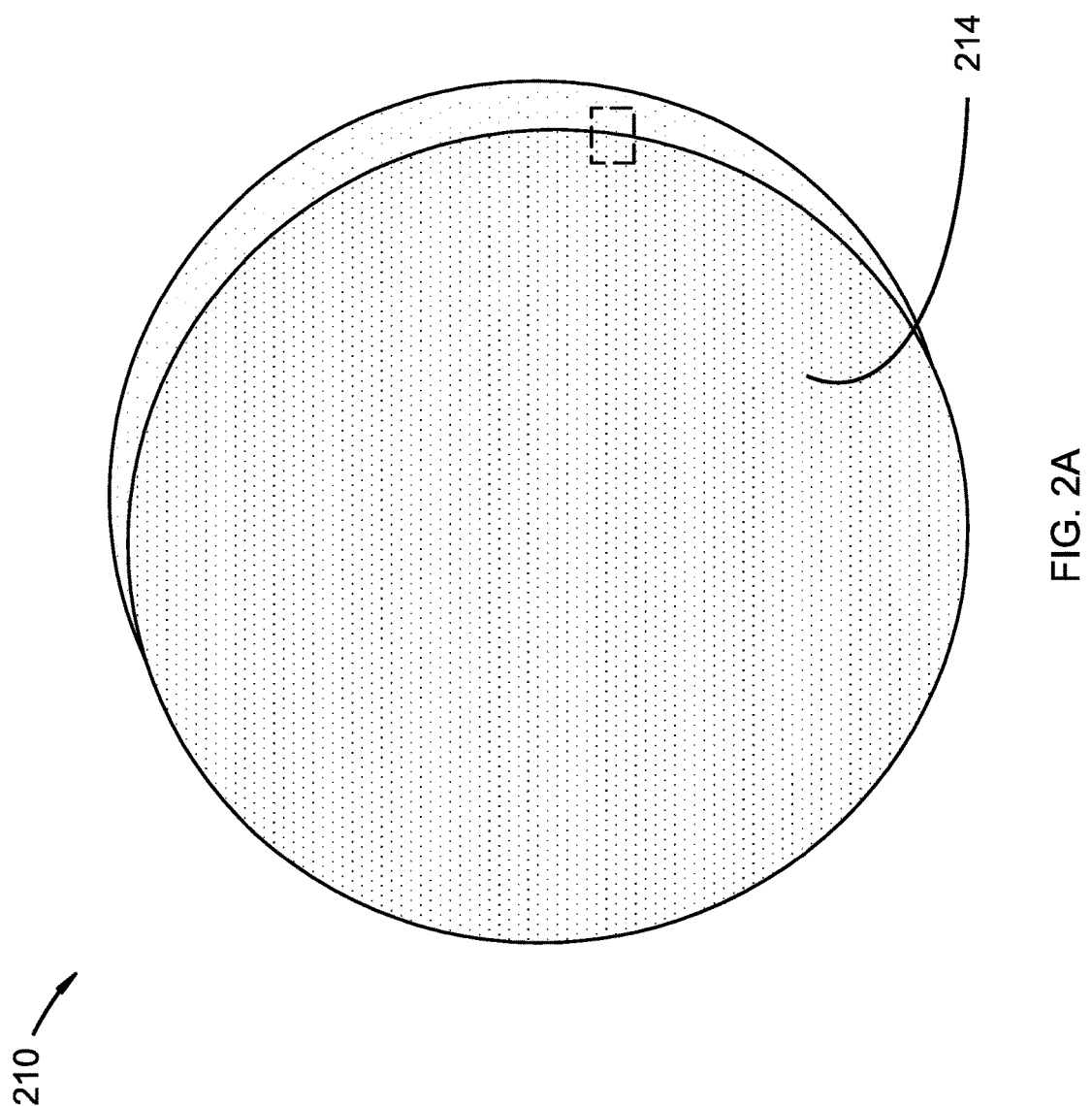
FIG. 2A depicts a gas permeable substrate.
Figure 2B:
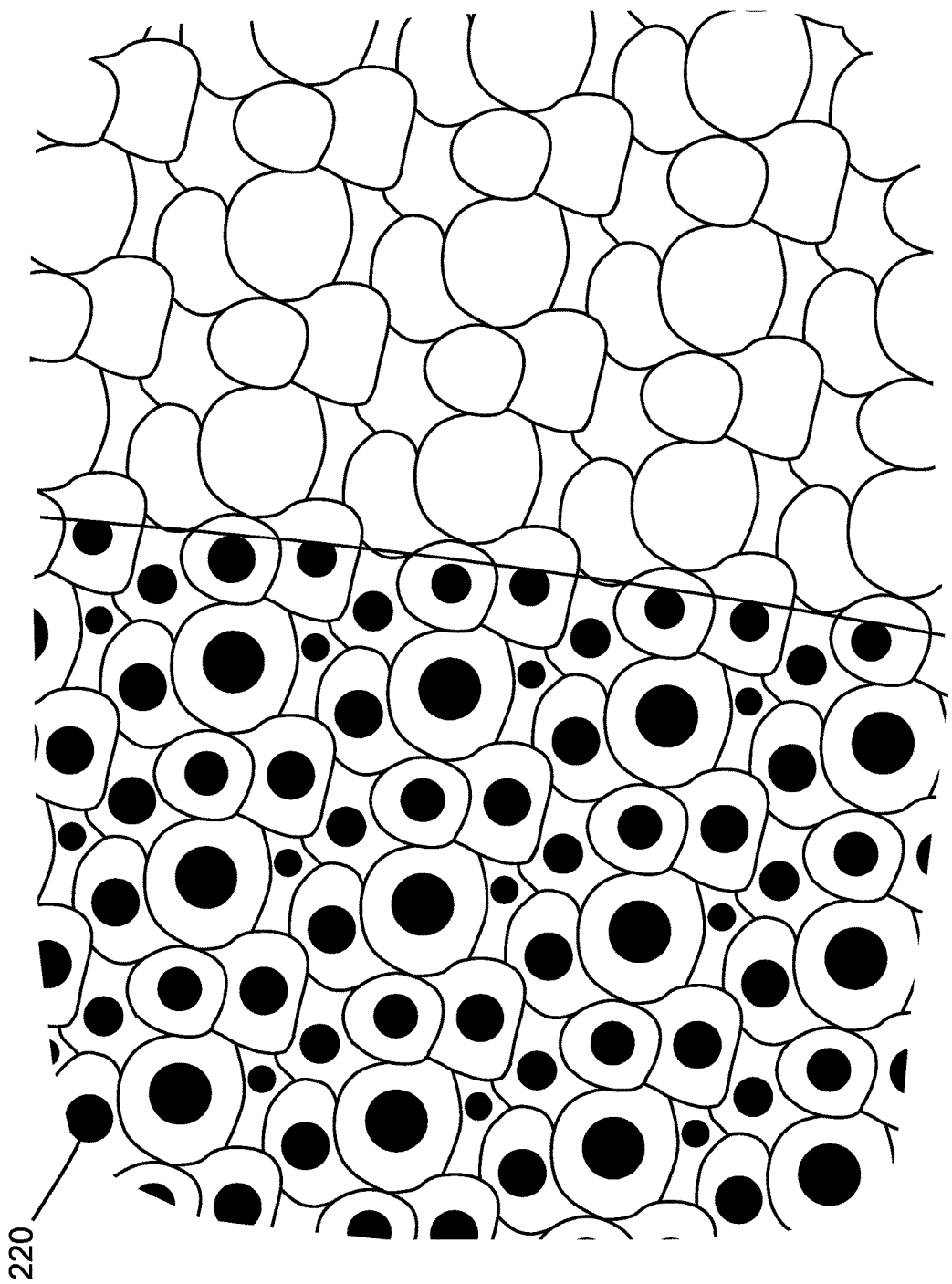
FIG. 2B depicts a detail view of a piece of the substrate from FIG. 2A.

FIG. 2A depicts a gas permeable substrate. FIG. 2B depicts a detail view of a piece of the substrate from FIG. 2A. Gas permeable substrate 210 includes first side 214 and a second side (not shown). First side 214 of gas permeable substrate 210 may be separated from the second side by a thickness. Gas permeable substrate 210 may also include a width which is more than twice the thickness of gas permeable substrate 210.

Sorbent media 220 may include pore structure on a submicron level. This may be advantageous because greater surface area may increase an amount of VOCs sorbent media 220 may adsorb.

Sorbent media 220 may be any of a variety of media, including activated charcoal, silica gel, zeolites, porous glass, clays, etc. In some embodiments, sorbent media 220 may be intercalated into or onto substrate 210 by dispersing sorbent media 220 into a liquid and passing the liquid containing sorbent media 220 through substrate 210. In some other embodiments, sorbent media 220 may be intercalated into or onto substrate 210 by pressing, rubbing, or air-blasting sorbent media 220 into or onto substrate 210. Air-blasting intercalation may be achieved by mixing sorbent media 220 with a pressurized gas, which mixture may be discharged at substrate 210.

In some embodiments where a flash lamp rapid desorption heater (depicted in FIG. 1B) is used to dump VOCs from gas permeable substrate 210, a majority of sorbent media 220 may be located on first side 214. This may enable sorbent media 220 to quickly absorb heat from the flash lamp heater in order to quickly dump any VOCs adsorbed by sorbent media 220.

Figure 3:
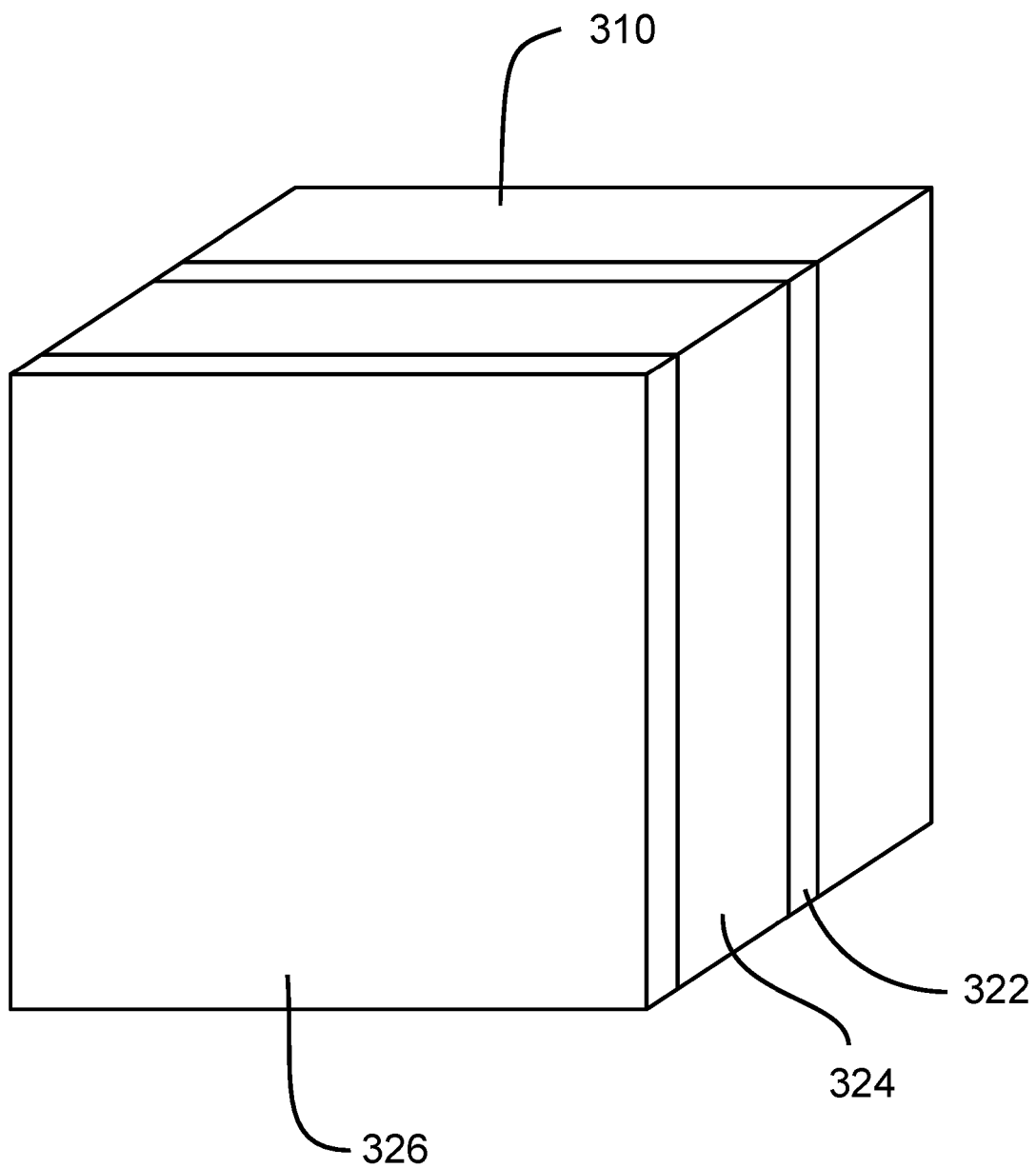
FIG. 3 depicts a perspective view of a gas permeable substrate.

FIG. 3 depicts a perspective view of a gas permeable substrate. Gas permeable substrate 310 includes sorbent media which may be intercalated into first sorbent-laden side 322. First sorbent-laden side 322 may be covered by gas permeable cover 324. Gas permeable cover 324 may include same material as gas permeable substrate 310. The material may include additional sorbent media 326 intercalated into gas permeable cover 324.

Additional sorbent media 326 and first sorbent-laden side 322 may face an upstream flow of a gas carrying VOCs. In some embodiments, VOCs may be collected by first sorbent-laden side 322 and additional sorbent media 326. First sorbent-laden side 322 may be intercalated with sorbent media having a different pore size than that of additional sorbent media 326. Gas permeable cover 324 may help retain sorbent media of first sorbent-laden side 322.

Figure 4A:
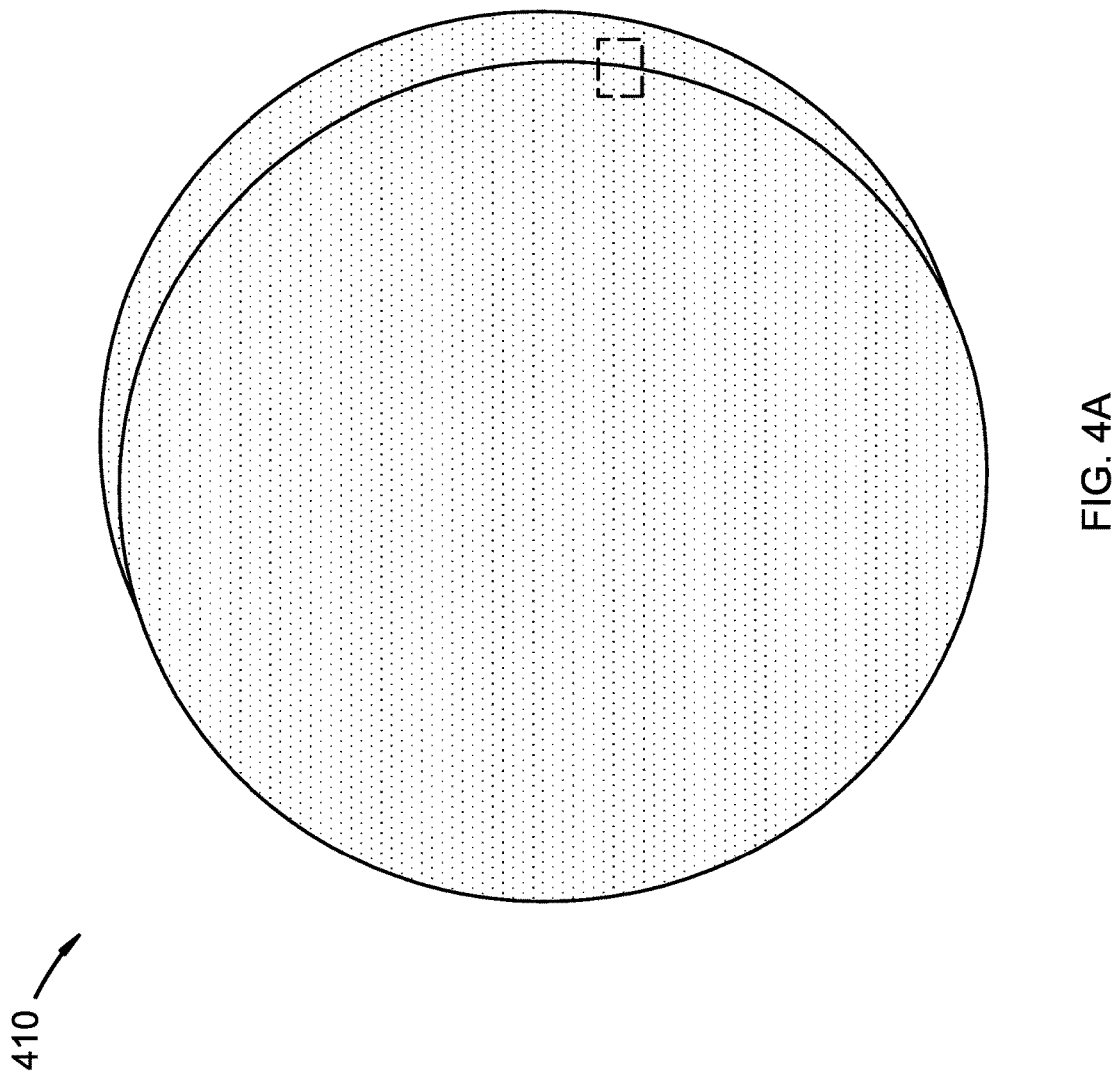
FIG. 4A depicts an embodiment similar to FIG. 2A with sorbent media.
Figure 4B:
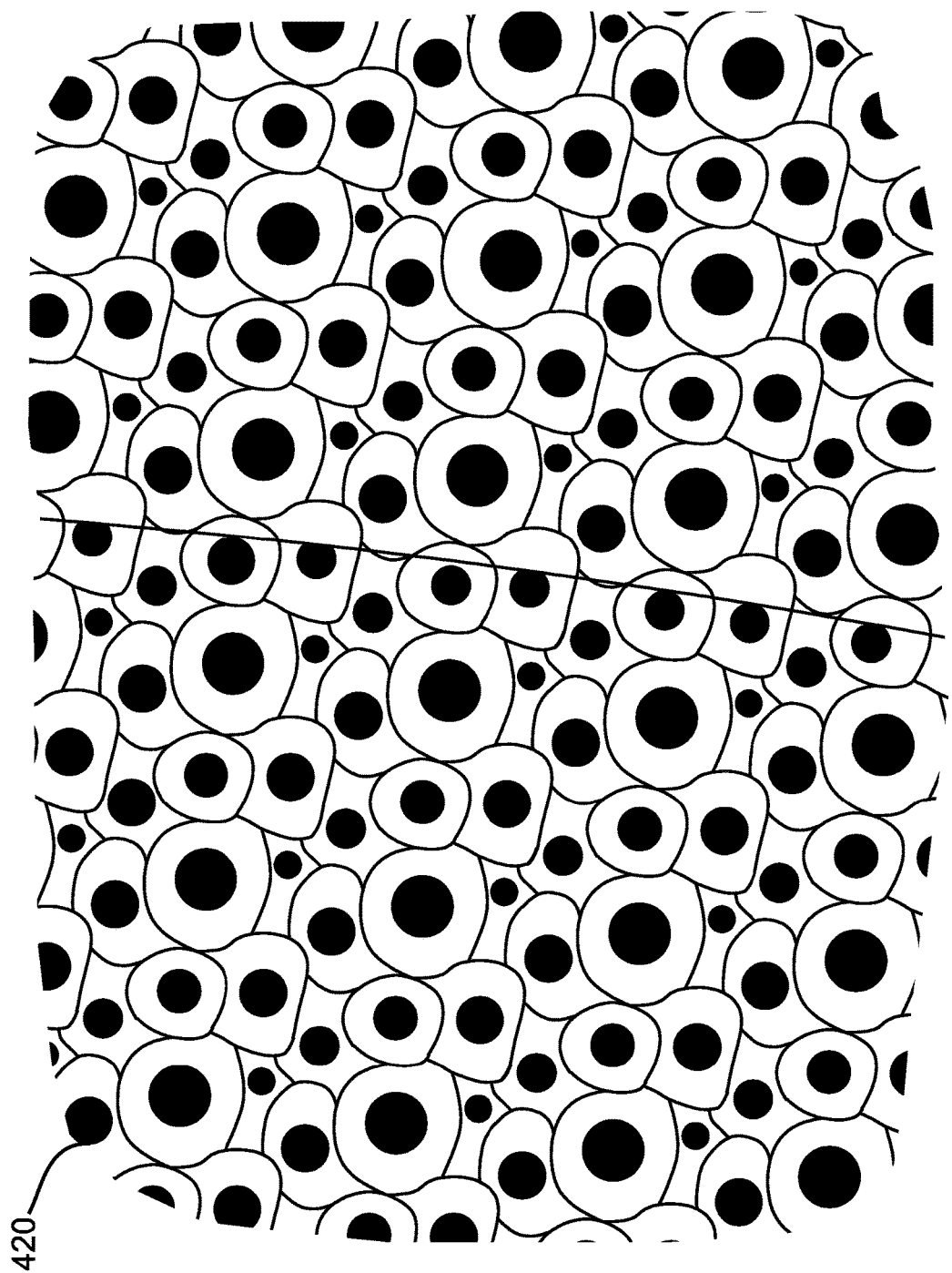
FIG. 4B depicts an embodiment similar to FIG. 2B with sorbent media.

FIG. 4A depicts an embodiment similar to FIG. 2A with sorbent media. FIG. 4B depicts an embodiment similar to FIG. 2B with sorbent media. Gas permeable substrate 410 may include sorbent media 420. Sorbent media 420 may be intercalated throughout gas permeable substrate 410. In some embodiments, due to sorbent media 420 being intercalated throughout gas permeable substrate 410, gas permeable substrate 410 may have a thickness which is at least half as thick as a width of gas permeable substrate 410. In some embodiments, sorbent media 420 may adsorb a large fraction of VOCs flowing through gas permeable substrate 410. In some further embodiments, due to the comparatively small thickness of gas permeable substrate 410, the large fraction of VOCs may be dumped quickly via using a rapid desorption heater.

FIG. 5 depicts a perspective view of a tubular gas permeable substrate. Gas permeable substrate 510 may have a tubular geometry. Gas permeable substrate 510 may include first side 526 and second side 528. First side 526 may be an outer surface and second side 528 may be an inner surface.

Gas permeable substrate 510 may include intercalated sorbent media. The sorbent media may be intercalated into first side 526 and/or second side 528. In some embodiments, gas permeable substrate 510 may be rotatable about an axis which may be concentric with tubular geometry of gas permeable substrate 510. Substrate 510 may also be rotatable about an axis perpendicular to gas flow 536. Gas flow 536 may be caused by a blower. Gas flow 536 may move gases, including VOCs, over or through gas permeable substrate 510. Substrate 510 may subsequently rotate about the axis aforementioned such that a surface on first side 526 which was previously facing upstream of gas flow 536 may face downstream. A rapid desorption heater may be located downstream of gas permeable substrate 510. The heater may activate such that any VOCs captured by sorbent media on first side 526 or second side 528 may be dumped simultaneously downstream without substrate 510 impeding flow of dumped VOCs.

In some embodiments, substrate 510 may rotate continuously such that first side 526 may capture VOCs more evenly. This in turn may enable substrate 510 to hold a greater amount of VOCs. In some embodiments, silica gel may be the sorbent media which may have a pore size from 2.4 nanometers to 6 nanometers. As pore size decreases, surface area of the sorbent media may tend to increase, thus increasing adsorbent capacity. Also, silica gel may attract amines, while using activated charcoal as the sorbent media may attract VOCs such as benzene, toluene, or xylene.

Figure 6:
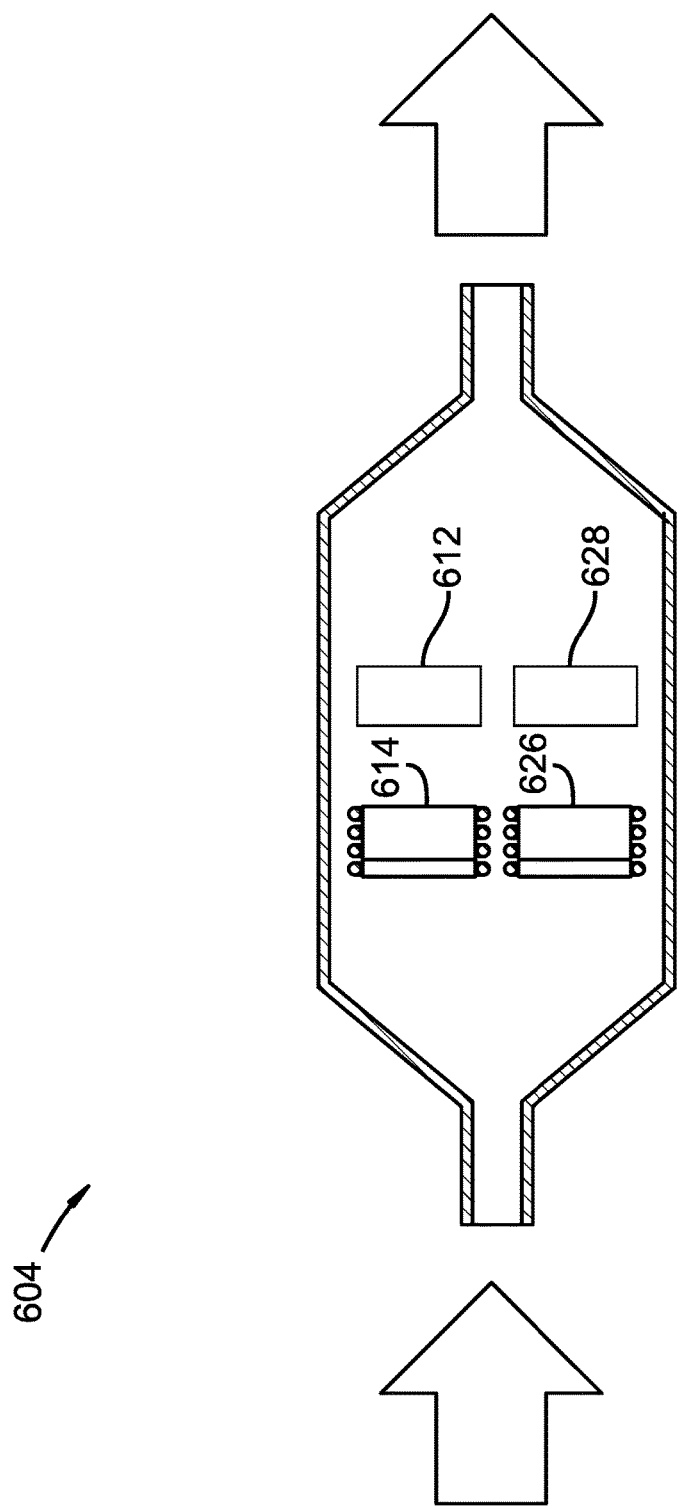
FIG. 6 depicts an embodiment similar to FIG. 1B with multiple gas permeable substrates.

FIG. 6 depicts an embodiment similar to FIG. 1B with multiple gas permeable substrates. Housing 604 may include first gas permeable substrate 614, second gas permeable substrate 626, first chemical sensor 612, and second chemical sensor 628. Second gas permeable substrate 626 may be placed in parallel with first gas permeable substrate 614. Second chemical sensor 628 may have a different chemical sensitivity than first chemical sensor 612. Also, second chemical sensor 628 may be placed in parallel with first chemical sensor 612.

Figure 7:
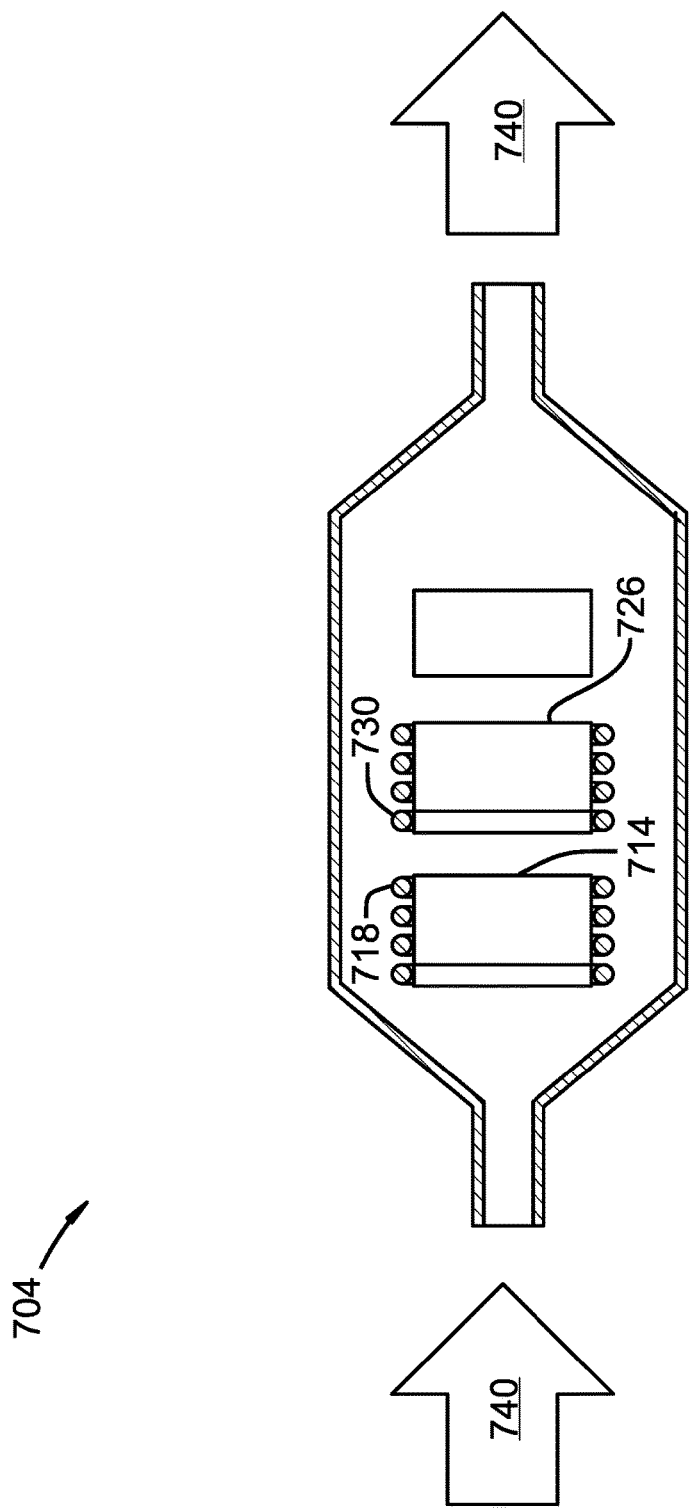
FIG. 7 depicts an embodiment similar to FIG. 1B with multiple gas permeable substrates in series.

FIG. 7 depicts an embodiment similar to FIG. 1B with multiple gas permeable substrates in series. Housing 704 may include first gas permeable substrate 714 and second gas permeable substrate 726. Second gas permeable substrate 726 may be placed in series with first gas permeable substrate 714. First gas permeable substrate 714 may include a first rapid desorption heater 718. Second gas permeable substrate 726 may include a second heater 730.

In some embodiments, gas flow 740 passes first gas permeable substrate 714, wherein first gas permeable substrate 714 may have a primary chemical sensitivity, such that only certain VOCs may adsorb to into sorbent media intercalated to/into first gas permeable substrate 714. Second gas permeable substrate 726 may also have a primary chemical sensitivity, such that second gas permeable substrate 726 may collect similar VOCs which correspond to its sensitivity. It may be that gas permeable substrate 726 may collect VOCs which pass by first substrate 714. For example, in some embodiments, first substrate 714 may become saturated with VOCs. In this case, it may be that second substrate 726 may collect more VOCs after first substrate 714 is saturated. This may allow a larger amount of VOCs to be collected. Subsequently, both or one of first substrate 714 and second substrate 726 may dump their collected VOCs via rapid desorption heater 718 or rapid desorption heater 730.

Figure 8:
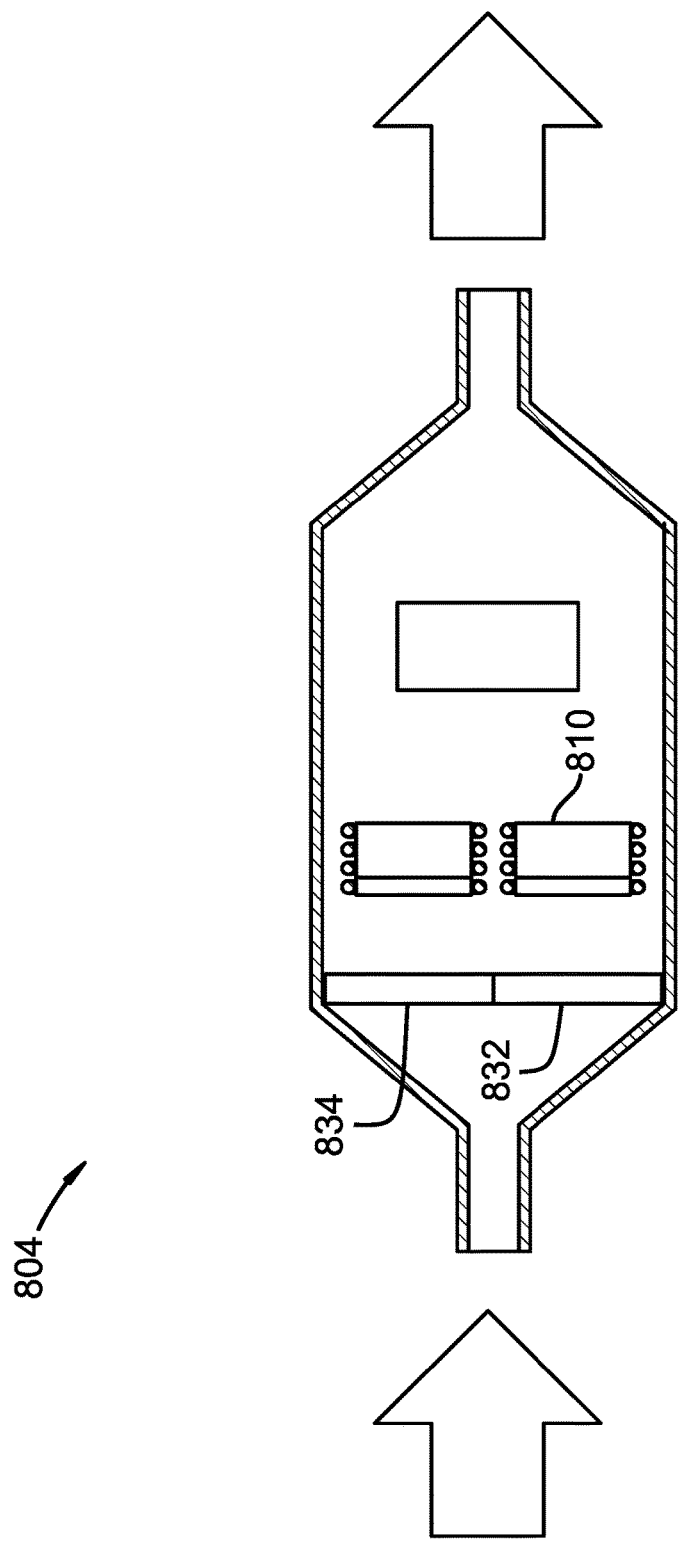
FIG. 8 depicts an embodiment similar to FIG. 6 with a chemical separator.

FIG. 8 depicts an embodiment similar to FIG. 6 with a chemical separator. Housing 804 may include gas permeable substrate 810 and chemical separator 832. Chemical separator 832 may include one or more molecular sieves such that certain chemicals may only pass through certain portions of chemical separator 832. In some embodiments, chemical separator 832 may span a width and thickness of housing 804. In some further embodiments, the width and thickness aforementioned may be great enough that any gasses which pass through housing 804 may be constrained to pass through chemical separator 832.

In some embodiments, chemical separator 832 may be a first chemical separator, and housing 804 may include multiple chemical separators, such as second chemical separator 834.

Figure 9:
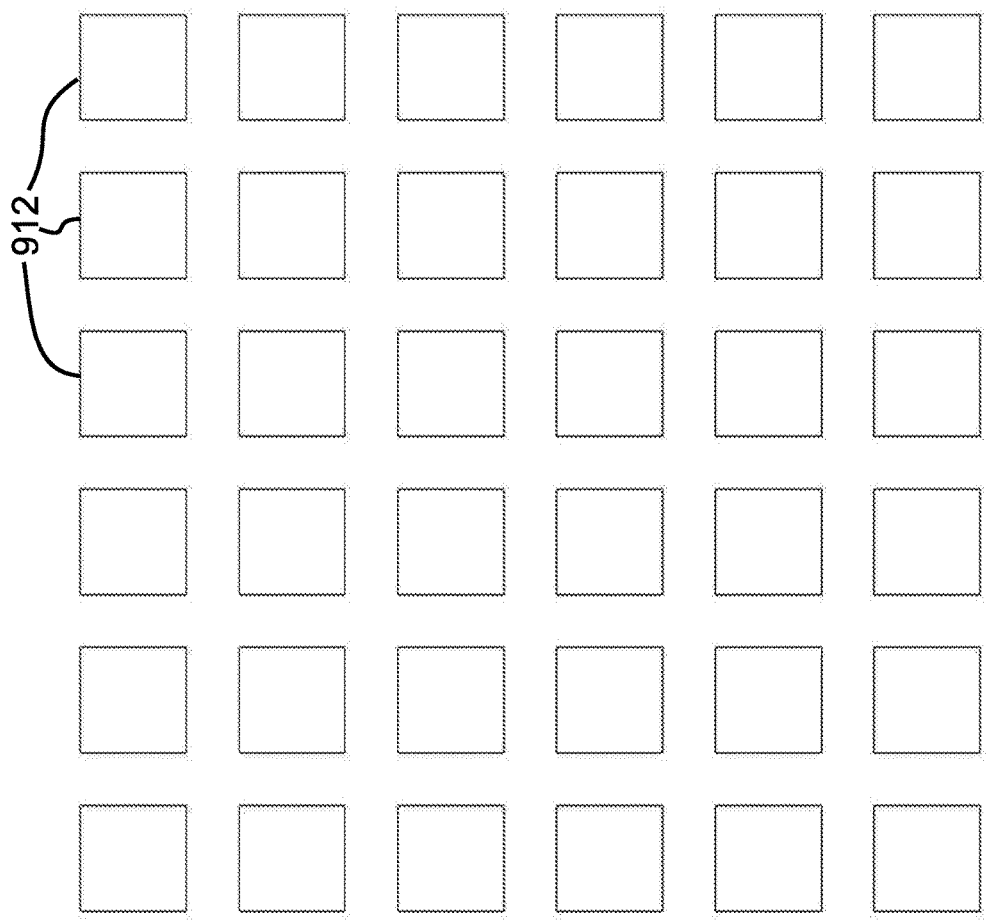
FIG. 9 depicts an array of chemical sensors.

FIG. 9 depicts an array of chemical sensors. Array of chemical sensors 938 may include chemical sensors 912 which may have differing chemical sensitivities. Chemical sensors 912 may be chemically sensitive on one or more planes perpendicular to a gas flow. In some embodiments, each of chemical sensors 912 may have a different chemical sensitivity such that a wide range of VOCs may be tested with them. VOCs may include any of a variety of chemicals such as carbon, hydrogen, oxygen, fluorine, chlorine, bromine, sulfur, nitrogen, or chemical products thereof.

Figure 10:
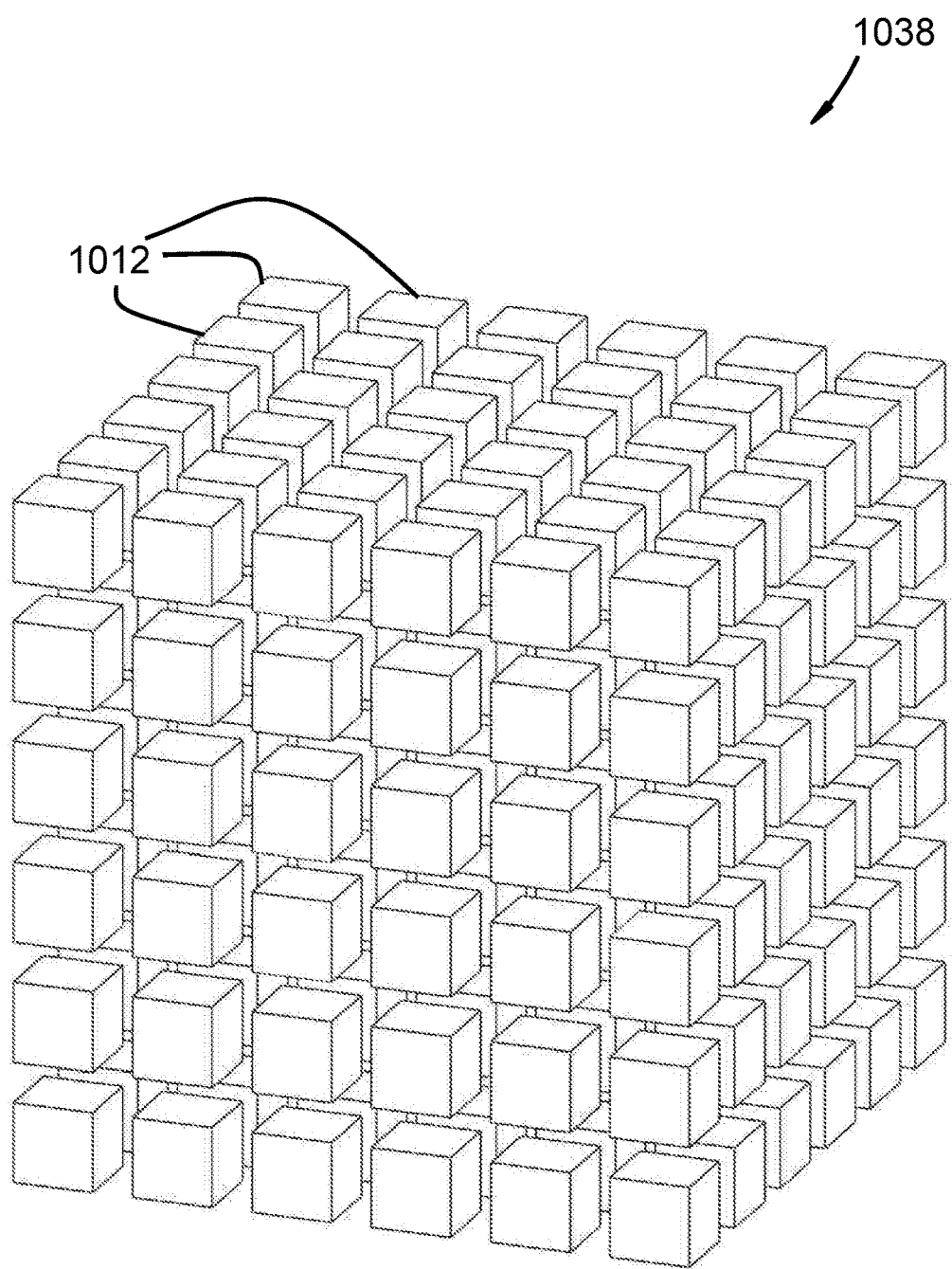
FIG. 10 depicts a perspective view of a three-dimensional array of chemical sensors.

FIG. 10 depicts a perspective view of a three-dimensional array of chemical sensors. Array of chemical sensors 1038 may include chemical sensors 1012. Chemical sensors 1012 may be chemically sensitive on one or more of their surfaces. For example, in some embodiments, chemical sensors 1012 may be chemically sensitive on surfaces parallel to a flow of gasses passing over or through them.

The invention claimed is:
1. A toilet apparatus comprising:
 a toilet bowl comprising multiple apertures and a blower, the blower fluidly connected to one or more of the apertures; and
 a housing fluidly connected to the blower, the housing comprising a gas permeable substrate and a gas chemical sensor, wherein the gas permeable substrate comprises a first side, a second side, intercalated sorbent media, and a desorption heater, wherein the desorption heater comprises a flash lamp heater.

\* \* \* \* \*